(12) United States Patent
Fitzpatrick

(10) Patent No.: US 7,786,180 B2
(45) Date of Patent: Aug. 31, 2010

(54) METHANOL SYNTHESIS

(75) Inventor: Terence James Fitzpatrick, Cleveland (GB)

(73) Assignee: Johnson Matthey PLC, London (GB)

(*) Notice: Subject to any disclaimer, the term of this patent is extended or adjusted under 35 U.S.C. 154(b) by 0 days.

(21) Appl. No.: 11/915,656

(22) PCT Filed: May 9, 2006

(86) PCT No.: PCT/GB2006/050096

§ 371 (c)(1),
(2), (4) Date: Nov. 27, 2007

(87) PCT Pub. No.: WO2006/126017

PCT Pub. Date: Nov. 30, 2006

(65) Prior Publication Data

US 2009/0018220 A1    Jan. 15, 2009

(30) Foreign Application Priority Data

May 27, 2005    (GB) .................................. 0510823.8

(51) Int. Cl.
*C07C 27/00* (2006.01)
(52) U.S. Cl. ................. 518/704; 518/705; 518/706; 518/712; 518/700
(58) Field of Classification Search .............. 518/700, 518/704, 705, 706, 712
See application file for complete search history.

(56) References Cited

U.S. PATENT DOCUMENTS

| | | | |
|---|---|---|---|
| 4,650,814 A | 3/1987 | Keller | |
| 4,788,175 A | 11/1988 | Short et al. | |
| 5,252,609 A * | 10/1993 | Pinto | 518/703 |
| 6,258,860 B1 * | 7/2001 | Weedon et al. | 518/706 |
| 6,387,963 B1 | 5/2002 | Fitzpatrick | |
| 6,433,029 B1 * | 8/2002 | Fitzpatrick | 518/706 |
| 6,486,219 B1 * | 11/2002 | Janda et al. | 518/706 |
| 7,470,811 B2 * | 12/2008 | Thiebaut | 562/519 |
| 2007/0259972 A1 * | 11/2007 | Lattner et al. | 518/700 |

FOREIGN PATENT DOCUMENTS

| | | |
|---|---|---|
| EP | 0 080 270 A2 | 6/1983 |
| EP | 0 081 948 B1 | 6/1983 |
| EP | 0 329 292 A2 | 8/1989 |
| EP | 1 060 788 A1 | 12/2000 |

* cited by examiner

*Primary Examiner*—Jafar Parsa
*Assistant Examiner*—Yate' K Cutliff
(74) *Attorney, Agent, or Firm*—RatnerPrestia

(57) ABSTRACT

A process for synthesising methanol comprises the steps of: (i) reforming a hydrocarbon feedstock and separating water to generate a make-up gas comprising hydrogen and carbon oxides, the make-up gas mixture having a stoichiometric number, R, $R=([H_2]-[CO_2])/([CO_2]+[CO])$ of less than 2.0, (ii) combining the make up gas with an unreacted synthesis gas to form a synthesis gas mixture, (iii) passing the synthesis gas through a bed of methanol synthesis catalyst to generate a product stream, (iv) cooling the product stream to recover a crude methanol stream from the unreacted synthesis gas, (v) removing a portion of the unreacted synthesis gas as a purge gas, and (vi) feeding the remaining unreacted synthesis gas to step (ii), wherein hydrogen is recovered from a portion of the purge gas and the make up gas, and the recovered hydrogen is included in the synthesis gas mixture.

12 Claims, 2 Drawing Sheets

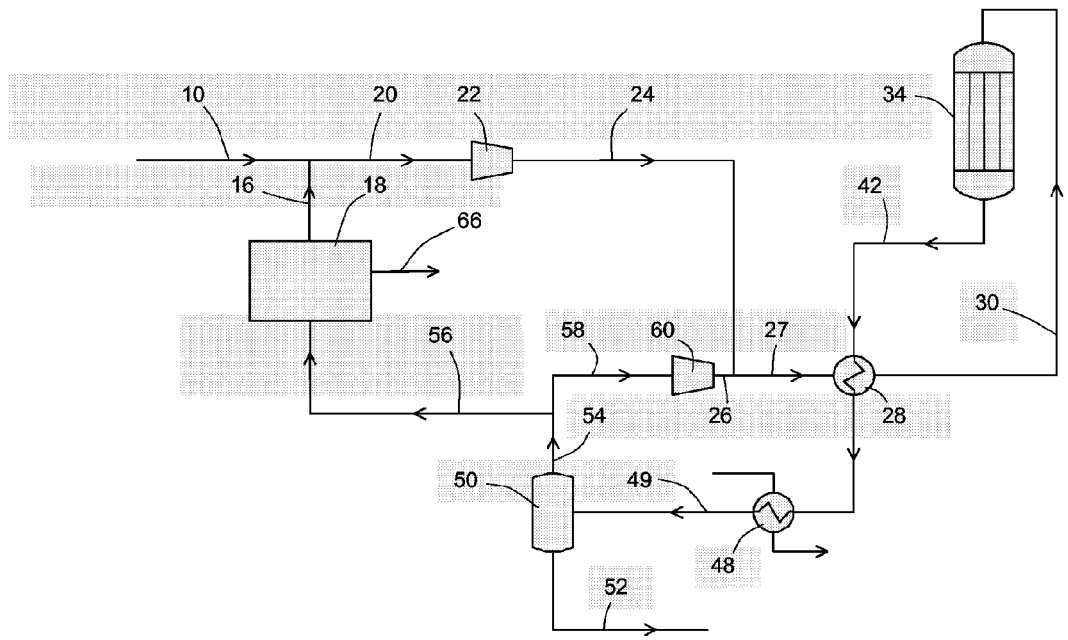
Figure 2 (Comparative)
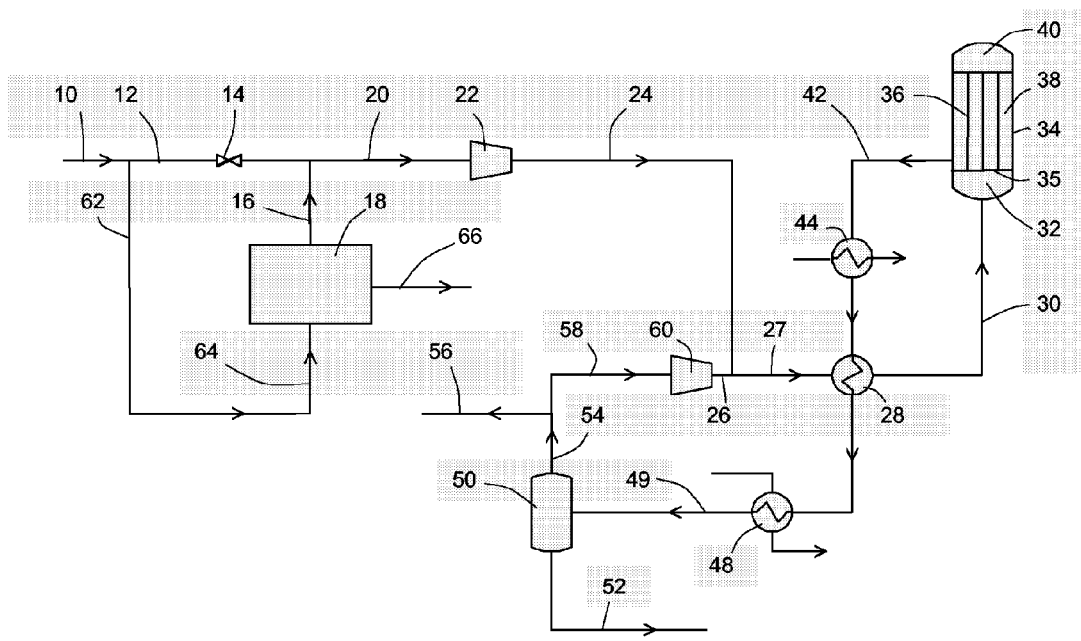
Figure 3 (Comparative)

METHANOL SYNTHESIS

CROSS-REFERENCE TO RELATED APPLICATION

This application is the U.S. National Phase application of PCT International Application No. PCT/GB2006/050096, filed May 9, 2006, and claims priority of British Patent Application No. 0510823.8, filed May 27, 2005.

FIELD OF THE INVENTION

This invention relates to methanol synthesis and in particular to methanol synthesis from a synthesis gas that is deficient in hydrogen.

BACKGROUND OF THE INVENTION

Methanol synthesis is generally performed by passing a synthesis gas comprising hydrogen, carbon oxides and any inert gases at an elevated temperature and pressure through one or more beds of a methanol synthesis catalyst, which is often a copper-containing composition. Methanol is generally recovered by cooling the product gas stream to below the dew point of the methanol and separating off the product as a liquid. The process is usually operated in a loop: thus the remaining unreacted gas stream is usually recycled to the synthesis reactor as part of the synthesis gas via a circulator. Fresh synthesis gas, termed make-up gas, is compressed and added to the recycled unreacted gas to form the synthesis gas stream. A purge stream is often taken from the circulating gas stream to avoid the build up of inert gases. Such a process is described for example in EP 0329292.

This arrangement is, however, unsuitable for gases whose stoichiometric number (R), defined by the formula;

$$R = \frac{[H_2] - [CO_2]}{[CO_2] + [CO]}$$

is less than 2, signifying that the gas is deficient in $H_2$ for the manufacture of methanol. Synthesis gases deficient in hydrogen may be obtained from reforming processes including a step of partial oxidation, such as autothermal reforming. In such a case, the hydrogen will be consumed in the methanol synthesis reaction while a substantial portion of the carbon oxides remain unreacted leading to a composition in the synthesis loop which has very high levels of carbon oxides but is low in hydrogen. This has several consequences, among them that the required catalyst volume will be high and that the level of by-products (higher alcohols and ketones in particular) will be much higher than normal.

It is known that hydrogen can be recovered from the purge gas stream using a hydrogen recovery unit and recycled back into the feed gas so that the gas within the synthesis loop is significantly more $H_2$-rich than is the synthesis gas. However, one of the difficulties with this approach is that for synthesis gases that are very deficient in $H_2$, it is necessary to recover large quantities of $H_2$ from the purge gas, and to have such a large flow of purge gas means either operating the synthesis loop at low pressure or having a low ratio of flow of recycle gas to flow of fresh synthesis gas. Running the synthesis loop at low pressure is not attractive for large commercial scale plants due to the size of the pipework, vessel diameters, etc., whereas running with a low recycle ratio can impose restrictions on the methanol synthesis reactor that may be unacceptable. For instance, a low recycle ratio means that using the circulating gas to cool the reaction, either in a quench cooled or tubular reactor, is impossible, so the only option is a steam-raising reactor. Furthermore, the low recycle ratio means that the reactant concentration at the inlet to the reactor is high as will be the reaction rates, so in order to prevent excessive temperatures in the catalyst bed, the catalyst will have to be installed inside the tubes of a tubular steam raising reactor. This is an unattractive choice as this leads to poor utilisation of the volume within the shell of the reactor as well as the requirement for extremely thick, heavy tube sheets. There is also a limit to the pressure at which steam can be raised, so utilisation of this steam may complicate the design of the steam system on such a plant so increasing cost and reducing operability and reliability.

Another alternative is to take a side-stream of the fresh synthesis gas, also termed make-up gas (MUG), recover hydrogen from it using a hydrogen recovery unit, and feed this hydrogen back into the synthesis gas. However, the drawback to this arrangement is that some hydrogen is lost within the hydrogen recovery unit before it ever gets to the synthesis loop, and the synthesis gas, after enrichment with this hydrogen, will now have a stoichiometry number greater than 2, so the purge gas will now consist of a significant portion of unreacted $H_2$. The effect of this is that the quantity of methanol produced from a fixed quantity of synthesis gas is reduced, and so a large synthesis gas generation unit is required for a given production capacity. Since the synthesis gas generation unit is the most expensive part of the plant, increased spending in this area is uneconomic.

Thus there is a need to provide a methanol synthesis process including a step of hydrogen recovery without the disadvantages of either method.

SUMMARY OF THE INVENTION

Accordingly the invention provides a process for synthesising methanol comprising the steps of;
(i) reforming a hydrocarbon feedstock and separating water from the resulting reformed gas mixture to generate a make-up gas comprising hydrogen and carbon oxides, said make-up gas mixture having a stoichiometric number, R, defined by the formula; $R=([H_2]-[CO_2])/([CO_2]+[CO])$ of less than 2.0,
(ii) combining said make up gas with an unreacted synthesis gas to form a synthesis gas mixture,
(iii) passing the synthesis gas mixture at elevated temperature and pressure through a bed of methanol synthesis catalyst to generate a product stream comprising methanol and unreacted synthesis gas,
(iv) cooling said product stream to recover a crude methanol stream from said unreacted synthesis gas,
(v) removing a portion of said unreacted synthesis gas as a purge gas, and
(vi) feeding the remaining unreacted synthesis gas to step (ii) characterised in that hydrogen is recovered from at least a portion of said purge gas and a portion of said make up gas, and the recovered hydrogen is included in the synthesis gas mixture.

BRIEF DESCRIPTION OF THE DRAWINGS

In the accompanying drawings:
FIG. 2 is a schematic representing a comparative example with partial hydrogen recovery from purge gas.
FIG. 3 is a schematic representing a comparative example with partial hydrogen recovery from make up gas.

DETAILED DESCRIPTION OF THE INVENTION

Figure 1:
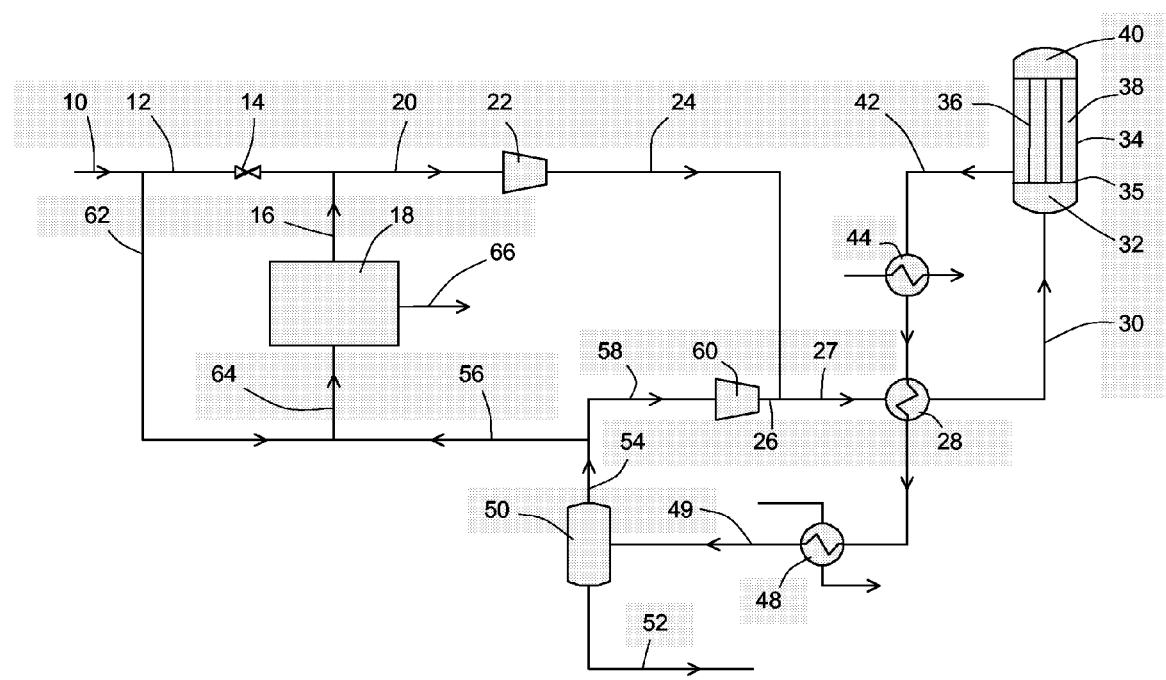
FIG. 1 is a schematic representing an embodiment of the present invention.

The make up gas comprising hydrogen and carbon oxides is obtained by reforming a hydrocarbon feedstock such as methane, natural gas, associated gas or naphtha and removing water from the resulting reformed gas mixture. The reforming process may comprise one or more steps of steam reforming and/or partial oxidation. For example, the reforming may comprise a step of primary steam reforming in which a hydrocarbon and steam, and optionally carbon dioxide, are passed through externally-heated catalyst-filled tubes in a combustion-fired or gas-heated reformer and a step of secondary reforming in which the primary reformed gases, optionally with further hydrocarbon, are subjected to a step of partial combustion with an oxygen-containing gas, preferably substantially pure oxygen, and the partially combusted gases passed through a bed of steam reforming catalyst. In one preferred embodiment, the secondary reformed gases are used to externally heat the catalyst-filled tubes of the primary reformer. Alternatively, the reforming process may comprise a step of autothermal reforming in which the hydrocarbon feedstock is fed to a reformer where it is first subjected to partial oxidation with an oxygen-containing gas and the resulting hot partially combusted gases passed through a bed of a steam reforming catalyst. Steam may be added to the hydrocarbon and/or oxygen-containing gas.

Primary steam reforming catalysts typically comprise nickel on a refractory support e.g. alumina or calcium aluminate. Secondary and autothermal steam reforming catalysts also typically comprise nickel on a refractory support. Alternatively a precious metal catalyst may be employed such as platinum, palladium and/or rhodium.

Additionally the reforming process may comprise one or more steps of adiabatic steam reforming over a bed of supported nickel steam reforming catalyst at temperatures between 450 and 650° C. Such adiabatic low-temperature steam reforming, often termed pre-reforming, has the advantage that higher hydrocarbons are converted to methane and some hydrogen is generated, thus reducing the possibility of carbon formation in the primary steam reformer or autothermal reformer, especially at low steam ratios.

The reformed gas mixture, depending on the reforming process used, may be at a temperature in the range 400-1150° C., a pressure of 10-30 bar abs and comprises different amounts of steam, hydrogen, carbon oxides, i.e. carbon monoxide and carbon dioxide, methane, and inert gases such as nitrogen and argon.

Make up gas is preferably obtained from the reformed gas mixture by cooling it to below the dew point of steam and separating condensed water from the gas mixture. Cooling may be performed by heat exchange with water to generate steam. The reformed gas mixture is preferably cooled to below 100° C., more preferably below 60° C. to condense water. The cooled mixture is preferably fed to a separator where the condensed water may be separated from the gas mixture. The separated water may usefully be recycled to generate steam for performing the reforming step.

Howsoever the make up gas is generated; it should have a stoichiometric number (R), defined by the formula;

$$R = \frac{[H_2] - [CO_2]}{[CO_2] + [CO]}$$

in which $[H_2]$, $[CO_2]$ and $[CO]$ are the concentrations of hydrogen, carbon dioxide and carbon monoxide respectively of less than 2.0, preferably less than 1.8. Thus it is deficient in hydrogen for the methanol synthesis step.

In the present invention a side-stream of make up gas is taken to hydrogen recovery. The remainder is fed to a methanol synthesis loop in which a synthesis gas mixture comprising make up gas and unreacted synthesis gas containing hydrogen and carbon oxides is fed to one or more steps of methanol synthesis by means of one or more circulators. The temperature and pressure of the make up gas are preferably adjusted to be suitable for methanol synthesis prior to feeding it to the methanol synthesis loop by means of compressors and heat exchangers known to those skilled in the art. The methanol synthesis may desirably be performed at pressures in the range 40-150, and more conveniently in the range 45-120, bar abs. The temperature of the synthesis catalyst is suitably in the range 160-300° C.; preferably the peak temperature is below 285° C. The synthesis gas preferably enters the catalyst bed at a temperature in the range 200-250° C. and leaves the beds at temperatures preferably in the range 220-260° C. Such temperatures provide for an acceptable methanol output rate (owing to favourable equilibrium) without producing the greater content of by-product impurities, and reduction in catalyst life, that would result from operation at higher temperatures.

The methanol synthesis catalyst is preferably a copper-based catalyst. Particularly suitable are catalysts containing copper and compounds, e.g. oxides of zinc, aluminium, chromium, titanium, zirconium, and/or magnesium. The catalyst may be in the form of pellets, tablets or extrudates. Particularly preferred catalysts are described in U.S. Pat. No. 4,788,175.

The methanol synthesis step may be carried out in a methanol synthesis reactor of the quench converter type or in a reactor in which the catalyst bed has immersed therein heat exchange tubes through which the synthesis gas passes en route to the catalyst bed, for example as described in EP 0080270. Alternatively there may be used a reactor of the tube-cooled type, for example as described in EP 0081948, where the exothermic heat of methanol synthesis is removed by a flow of coolant, particularly water, through coolant tubes disposed in the catalyst bed or beds. Alternatively the tube-cooled catalyst bed may be disposed in a reaction vessel as an annular bed with synthesis gas inlet means adjacent the outer periphery of the bed and reacted synthesis gas outlet means adjacent the axis of the vessel, so that the synthesis gas flows radially inwards through the catalyst bed, i.e. in a radial flow reactor. In a radial flow arrangement, the coolant tubes will generally be disposed in planes perpendicular to the vessel axis. An example of a suitable radial flow reactor design is shown in EP 1060788.

By passing the synthesis gas mixture at elevated temperature and pressure through a bed of methanol synthesis catalyst, a product stream comprising methanol and unreacted synthesis gas is generated.

Methanol is recovered by cooling the product stream to condense crude methanol, which contains water and small amounts of higher alcohols and other compounds, from unreacted synthesis gas. The crude methanol may then be used but is preferably sent to one or more distillation steps in which pure methanol is separated from the water, higher alcohols and other by-products.

Because the methanol synthesis step consumes hydrogen and carbon oxides the unreacted synthesis gas can become enriched in inert gases such as nitrogen and argon, which are impurities in the hydrocarbon and/or oxygen-containing gas. Unreacted methane from the reforming step may also build up. The build up of such gases is undesirable and therefore a portion of the unreacted synthesis gas is removed as a purge gas. The amount of purge gas will depend on the exact flow-sheet. Preferably the remaining unreacted synthesis gas is compressed prior to mixing it with the make up gas. The resulting synthesis gas mixture is preferably heated prior to feeding it to the methanol synthesis reactor.

In the present invention hydrogen is recovered from at least a portion of the purge gas and from a portion of make up gas and said recovered hydrogen is included in the synthesis gas mixture fed to the methanol synthesis reactor. The purge and make up gases comprise hydrogen and carbon oxides as well as small amounts of unreacted methane and inerts. Hydrogen may be recovered from these gases, which may or may not be combined beforehand, using one or more hydrogen recovery units. Such units are known and may function by so-called pressure-swing absorption (PSA) in which an absorbent material is disposed in the unit that captures the non-hydrogen components of the gas stream, thereby allowing a gas rich in hydrogen to pass through. The advantage of a PSA hydrogen recovery unit is that the gas rich in hydrogen is recovered at the PSA operating pressure and the waste gas, which may be used as fuel, is recovered at low pressure. A disadvantage is that the absorbent has to be periodically cleansed of captured material by adjusting (i.e. lowering) the pressure in the unit. An alternative to PSA hydrogen recovery is a membrane hydrogen recovery unit, which functions continuously. The membrane functions by allowing the hydrogen to pass through while holding back non-hydrogen components of the gas stream fed to it. The membrane recovery unit however recovers a gas stream rich in hydrogen at a reduced pressure below that of the partial pressure of hydrogen in the feed stream to the unit, whereas the waste gas is recovered at the membrane operating pressure.

Accordingly, where a PSA hydrogen recovery unit is employed, the recovered hydrogen may either be fed to the make-up gas prior to its addition to the synthesis loop, or the recovered hydrogen may be fed directly to the synthesis loop by adding it to either the unreacted synthesis gas before or after the purge stream has been removed or to the synthesis gas mixture (comprising the combined make up gas and unreacted synthesis gas). In contrast, where the hydrogen recovery unit is a membrane recovery unit, the recovered hydrogen is preferably fed to the make-up gas stream destined for the synthesis loop prior to its compression. In a preferred process, the recovered hydrogen is fed to the make up gas. The resulting hydrogen-adjusted make up gas is then compressed, fed to the synthesis loop where it is mixed with the remaining unreacted synthesis gas, i.e. after the purge stream has been removed, heated and fed to the methanol synthesis reactor.

Adding hydrogen increases the value of R in the synthesis gas mixture towards the optimum stoichiometry value for methanol synthesis. Preferably the quantity of hydrogen added raises the value of R towards 2.0, preferably up to 2.2, especially to 2.1±0.1.

The quantity of hydrogen recovered from the purge gas or make up gas may be varied depending upon the precise flowsheet adopted and the contents of hydrogen and carbon oxides in the make up gas provided by the reforming stage. For example the purge gas may provide between 5 and 95% of the required hydrogen on a molar basis to bring the value of R towards 2.0 and the make up gas consequently between 95 and 5%. Preferably all the purge gas is fed to the hydrogen recovery unit, more preferably to provide >50% on a molar basis of the required hydrogen, with the remainder provided by the make up gas stream. Thus in a preferred arrangement, the purge gas is routed to the hydrogen recovery unit and this hydrogen source is supplemented with a side-stream of the make-up gas.

Preferably the side-stream of make up gas fed to the hydrogen recovery unit comprises <20%, preferably ≦10% by volume of the make up gas provided by the reforming stage. Hence preferably >80%, more preferably ≧90% by volume of the make up gas is fed to the synthesis loop. In this way, the design of the synthesis loop can be set to allow the most appropriate equipment to be selected, while still maintaining a very high level of conversion of hydrogen to methanol.

The invention is illustrated by reference to the accompanying drawings in which FIG. 1 depicts a flow sheet of a preferred embodiment of the present invention wherein hydrogen is recovered from combined purge gas and make up gas side-stream using a membrane recovery unit, and fed to the remaining make up gas, which is then compressed and fed to the synthesis loop. FIGS. 2 and 3 by way of comparison depict flowsheets not according to the present invention in which only partial hydrogen recovery either from purge gas or make up gas is affected.

In FIG. 1, make up gas supplied via line 10 divided into two portions. A first portion 12, controlled by valve 14 is combined with a hydrogen stream 16 fed from PSA hydrogen recovery unit 18 and the combined gases passed via a line 20 to compressor 22 where their pressure is increased before feeding them via line 24 to compressed unreacted synthesis gas in line 26. The combined synthesis gas is fed via line 27 to heat exchanger 28 where it is heated then fed via line 30 to the inlet zone 32 of a methanol synthesis reactor 34 defined by the reactor walls and tubesheet 35. The synthesis gas passes up though a plurality of tubes 36 extending from tubesheet 35 upwards through a bed of a particulate copper/zinc/alumina synthesis catalyst 38 into a space 40 above the bed and thence down through the bed to an outlet zone above tubesheet 35. Methanol synthesis takes place as the gases pass down through the catalyst bed and the resulting product stream is fed from the outlet zone via line 42 to heat exchanger 44 where it is used to raise steam, thence to the heat exchanger 28 where it is used to heat the synthesis gas and then heat exchanger 48 where it is cooled with cold water to condense crude methanol. The cooled mixture is fed via line 49 to separator 50 that separates the crude methanol via line 52 from unreacted synthesis gas in line 54. A purge stream 56 is taken from line 54 and the remaining unreacted synthesis gas is fed via line 58 to compressor 60. The compressed unreacted synthesis gas leaves compressor 60 via line 26 and is combined with the make up gas from line 24. The second make up gas stream 62 taken from line 10 is combined with the purge gas stream 56 and the combined stream fed via line 64 to the PSA recovery unit 18. Waste gases depleted in hydrogen are removed from the hydrogen recovery unit 18 via line 66.

In FIG. 2 (comparative) there is hydrogen recovery from purge gas stream 56 only. Thus purge gas stream 56 passes to the hydrogen recovery unit 18, make up gas stream 62 is absent and the recovered hydrogen 16 is added to stream 10. In this case the synthesis reactor is necessarily a steam-raising converter with pressurised-water cooling within the bed and therefore heat exchanger 44 is omitted. In this flowsheet, it is necessary to use a steam raising converter rather than the smaller, cheaper tube-cooled converted used in FIG. 1, because the circulation ratio of synthesis gas is too low to permit effective use of the TCC. This is because a larger amount as purge gas has to be removed to provide the required hydrogen.

In FIG. 3 (comparative) there is hydrogen recovery from make up gas via stream 62 only. Purge gas in line 56 is simply combusted. The synthesis reactor is according to that in FIG. 1 and accordingly heat exchanger 44 is again present to cool the product stream 42 before it passes to heat exchanger 28.

EXAMPLES

The invention is further illustrated by reference to the following calculated examples.

EXAMPLE 1

According to the embodiment depicted in FIG. 1.

| Stream | 10 | 62 | 16 | 20 | 30 | 42 | 58 | 56 | 52 |
|---|---|---|---|---|---|---|---|---|---|
| Temperature [C.] | 45.0 | 45.0 | 45.0 | 44.9 | 220.0 | 255.0 | 45.0 | 45.0 | 45.0 |
| Pressure [bar] | 34.0 | 34.0 | 34.0 | 34.0 | 81.5 | 80.0 | 77.7 | 77.7 | 77.7 |
| Molar Flow [kgmole/h] | 15210.6 | 1181.0 | 1336.8 | 15366.4 | 75366.4 | 66877.1 | 60000.0 | 1583.1 | 5294.2 |
| Mass Flow [kg/h] | 186073 | 14447 | 2695 | 174321 | 844492 | 844487 | 670171 | 17683 | 156637 |
| Hydrogen | 63.63% | 63.63% | 100.00% | 66.79% | 59.86% | 53.50% | 58.08% | 58.08% | 0.24% |
| CO | 24.71% | 24.71% | 0.00% | 22.56% | 7.61% | 3.49% | 3.79% | 3.79% | 0.09% |
| $CO_2$ | 7.21% | 7.21% | 0.00% | 6.58% | 5.88% | 5.37% | 5.70% | 5.70% | 1.49% |
| Methane | 3.15% | 3.15% | 0.00% | 2.88% | 19.46% | 21.93% | 23.70% | 23.70% | 1.27% |
| Nitrogen | 0.79% | 0.79% | 0.00% | 0.72% | 5.44% | 6.13% | 6.64% | 6.64% | 0.11% |
| Argon | 0.17% | 0.17% | 0.00% | 0.15% | 1.11% | 1.25% | 1.35% | 1.35% | 0.04% |
| Methanol | 0.00% | 0.00% | 0.00% | 0.00% | 0.53% | 6.95% | 0.67% | 0.67% | 79.97% |
| $H_2O$ | 0.34% | 0.34% | 0.00% | 0.31% | 0.11% | 1.38% | 0.06% | 0.06% | 16.78% |

Methanol production is high using a low volume of synthesis catalyst.

COMPARATIVE EXAMPLES

A) $H_2$ Recovery from Purge Gas Stream Only (FIG. 2)

| Stream | 10 | 16 | 20 | 30 | 42 | 58 | 56 | 52 |
|---|---|---|---|---|---|---|---|---|
| Temperature [C.] | 45.0 | 45.0 | 44.8 | 220.0 | 255.0 | 45.0 | 45.0 | 45.0 |
| Pressure [bar] | 34.0 | 34.0 | 34.0 | 81.5 | 80.0 | 77.7 | 77.7 | 77.7 |
| Molar Flow [kgmole/h] | 15210.6 | 4410.1 | 19620.7 | 41543.7 | 33535.7 | 21923.0 | 6918.8 | 4694.0 |
| Mass Flow [kg/h] | 186073 | 8891 | 194964 | 361988 | 361984 | 167025 | 52712 | 142248 |
| Hydrogen | 63.63% | 100.00% | 71.80% | 75.96% | 68.57% | 79.68% | 79.68% | 0.35% |
| CO | 24.71% | 0.00% | 19.16% | 11.34% | 3.76% | 4.35% | 4.35% | 0.11% |
| $CO_2$ | 7.21% | 0.00% | 5.59% | 6.12% | 5.94% | 6.59% | 6.59% | 1.90% |
| Methane | 3.15% | 0.00% | 2.44% | 4.67% | 5.79% | 6.67% | 6.67% | 0.39% |
| Nitrogen | 0.79% | 0.00% | 0.61% | 1.20% | 1.48% | 1.72% | 1.72% | 0.03% |
| Argon | 0.17% | 0.00% | 0.13% | 0.25% | 0.31% | 0.36% | 0.36% | 0.01% |
| Methanol | 0.00% | 0.00% | 0.00% | 0.31% | 12.33% | 0.60% | 0.60% | 84.42% |
| $H_2O$ | 0.34% | 0.00% | 0.26% | 0.14% | 1.82% | 0.04% | 0.04% | 12.78% |

B) $H_2$ Recovery from MUG Only (FIG. 3)

| Stream | 10 | 62 | 16 | 20 | 30 | 42 | 58 | 56 | 52 |
|---|---|---|---|---|---|---|---|---|---|
| Temperature [C.] | 45.0 | 45.0 | 45.0 | 44.9 | 220.0 | 255.0 | 45.0 | 45.0 | 45.0 |
| Pressure [bar] | 34.0 | 34.0 | 34.0 | 34.0 | 81.5 | 80.0 | 77.7 | 77.7 | 77.7 |
| Molar Flow [kgmole/h] | 15210.6 | 2162.1 | 1100.6 | 14149.0 | 89149.0 | 81157.8 | 75000.0 | 1142.2 | 5015.7 |
| Mass Flow [kg/h] | 186073 | 26449 | 2219 | 161842 | 1081684 | 1081680 | 919842 | 14009 | 147834 |
| Hydrogen | 63.63% | 63.63% | 100.00% | 66.46% | 53.53% | 47.95% | 51.09% | 51.09% | 0.21% |
| CO | 24.71% | 24.71% | 0.00% | 22.79% | 6.74% | 3.49% | 3.71% | 3.71% | 0.09% |
| $CO_2$ | 7.21% | 7.21% | 0.00% | 6.65% | 5.32% | 4.83% | 5.06% | 5.06% | 1.30% |
| Methane | 3.15% | 3.15% | 0.00% | 2.91% | 25.06% | 27.53% | 29.24% | 29.24% | 1.54% |
| Nitrogen | 0.79% | 0.79% | 0.00% | 0.73% | 7.21% | 7.92% | 8.43% | 8.43% | 0.14% |
| Argon | 0.17% | 0.17% | 0.00% | 0.15% | 1.45% | 1.59% | 1.70% | 1.70% | 0.05% |
| Methanol | 0.00% | 0.00% | 0.00% | 0.00% | 0.59% | 5.57% | 0.70% | 0.70% | 79.50% |
| $H_2O$ | 0.34% | 0.34% | 0.00% | 0.31% | 0.10% | 1.12% | 0.07% | 0.07% | 17.16% |

The calculations demonstrate that in the case of hydrogen recovery from the purge gas only, the excess carbon oxides are being eliminated from a gas stream that is relatively low in carbon oxides and so large quantities of hydrogen are being lost with the waste gas leading to a lower methanol production rate. Furthermore in the flowsheet of FIG. 2, a more complex, and therefore more expensive steam-raising converter is required. In the case of hydrogen recovery from MUG only, hydrogen is being lost with the waste gas from the hydrogen recovery unit as well as being lost in the purge gas stream. Again, the high hydrogen loss leads to lower methanol production.

Furthermore, calculations also demonstrate that if no hydrogen recovery is affected, compared to the flowsheet depicted in FIG. 1, the process requires 75% higher catalyst volume due to the low partial pressure of hydrogen and results in 3× higher by-products due to the high CO:H$_2$ ratio. Thus hydrogen recovery according to the present invention is able to reduce the catalyst volume and amount of waste product, therefore reducing the size of reaction vessels and simplifying purification of the crude methanol, which reduces the overall cost of the process.

The invention claimed is:

1. A process for synthesising methanol comprising the steps of;
   (i) reforming a hydrocarbon feedstock and separating water from the resulting reformed gas mixture to generate a make up gas comprising hydrogen and carbon oxides, said make up gas mixture having a stoichiometric number, R, defined by the formula; $R=([H_2]-[CO_2])/([CO_2]+[CO])$ of less than 2.0,
   (ii) forming a synthesis gas mixture consisting of said make up gas, an unreacted synthesis gas and a hydrogen stream,
   (iii) passing the synthesis gas mixture at elevated temperature and pressure through a bed of methanol synthesis catalyst to generate a product stream comprising methanol and unreacted synthesis gas,
   (iv) cooling said product stream to recover a crude methanol stream from said unreacted synthesis gas,
   (v) removing a portion of said unreacted synthesis gas as a purge gas, and
   (vi) feeding the remaining unreacted synthesis gas to step (ii)
   wherein hydrogen is recovered using a hydrogen recovery unit from at least a portion of said purge gas and a portion of said make up gas, and the recovered hydrogen is included in the synthesis gas mixture.

2. A process according to claim 1 wherein the hydrogen recovery unit is a pressure swing hydrogen recovery unit.

3. A process according to claim 1 wherein the hydrogen recovery unit is a membrane hydrogen recovery unit.

4. A process according to claim 2 wherein the recovered hydrogen is added to said unreacted synthesis gas or added to the make up gas that is combined with said unreacted synthesis gas.

5. A process according to claim 3 wherein the recovered hydrogen is fed to the make up gas that is combined with said unreacted synthesis gas.

6. A process according to claim 1 wherein the bed of methanol synthesis catalyst is disposed in a reactor in which the catalyst bed is cooled by the synthesis gas mixture passing through tubes disposed within the catalyst bed.

7. A process according to claim 1 wherein the product stream is cooled in separate stages of heat exchange with water under pressure.

8. A process according to claim 1 wherein the purge gas provides between 5 and 95% of the required hydrogen on a molar basis to bring the value of R towards 2.0.

9. A process according to claim 1 wherein all the purge gas is fed to the hydrogen recovery unit.

10. A process according to claim 1 wherein the amount of make up gas fed to the hydrogen recovery unit comprises <20% by volume of the make up gas provided by the reforming stage.

11. A process according to claim 1 wherein the reforming step is performed by autothermal reforming.

12. A process according to claim 1 wherein the crude methanol is distilled to obtain a substantially pure methanol product.

* * * * *